(12) United States Patent
Jo et al.

(10) Patent No.: US 11,207,295 B2
(45) Date of Patent: Dec. 28, 2021

(54) USE OF CARBAMATE COMPOUND FOR PREVENTING OR TREATING TRIGEMINAL NEURALGIA

(71) Applicant: SK BIOPHARMACEUTICALS CO., LTD., Gyeonggi-do (KR)

(72) Inventors: Min Jae Jo, Gyeonggi-do (KR); Sun Gwan Hwang, Gyeonggi-do (KR); Han Ju Yi, Gyeonggi-do (KR)

(73) Assignee: SK BioPharmaceuticals Co., Ltd., Seongnam-si (KR)

( * ) Notice: Subject to any disclaimer, the term of this patent is extended or adjusted under 35 U.S.C. 154(b) by 0 days.

(21) Appl. No.: 16/302,860

(22) PCT Filed: May 18, 2017

(86) PCT No.: PCT/KR2017/005172
§ 371 (c)(1),
(2) Date: Nov. 19, 2018

(87) PCT Pub. No.: WO2017/200317
PCT Pub. Date: Nov. 23, 2017

(65) Prior Publication Data
US 2019/0175555 A1 Jun. 13, 2019

(30) Foreign Application Priority Data
May 19, 2016 (KR) .................. 10-2016-0061386

(51) Int. Cl.
*A61K 31/41* (2006.01)
*A61P 25/02* (2006.01)
*A61K 31/16* (2006.01)
*A61K 9/00* (2006.01)

(52) U.S. Cl.
CPC .............. *A61K 31/41* (2013.01); *A61K 9/00* (2013.01); *A61K 31/16* (2013.01); *A61P 25/02* (2018.01)

(58) Field of Classification Search
CPC .......... A61K 31/41; A61K 31/16; A61K 9/00; A61P 25/02
See application file for complete search history.

(56) References Cited

U.S. PATENT DOCUMENTS 3,415,840 A 12/1968 Wolf
2006/0258718 A1* 11/2006 Choi .................... C07D 249/04
514/359
2010/0323410 A1 12/2010 Lim et al.
2011/0111467 A1 5/2011 Lim et al.
2014/0349969 A1* 11/2014 Penninger ............ A61K 31/435
514/81

FOREIGN PATENT DOCUMENTS

| JP | 2006-342079 A | 12/2006 |
| KR | 101286499 B1 | 7/2013 |
| WO | WO-2006/112685 A1 | 10/2006 |
| WO | WO-2010/150946 A1 | 12/2010 |
| WO | WO-2011/046380 A2 | 4/2011 |
| WO | WO-2015/171004 A1 | 11/2015 |

OTHER PUBLICATIONS

Sergio Canavero and Vincenzo Bonicalzi, Drug therapy of trigeminal neuralgia, Expert Rev. Neurotherapeutics 6(3), 429-440 (2006) (Year: 2006).*
Aydede, M. (2017) "Defending the IASP Definition of Pain.", *To appear in The Monist*, 100(4):1-31, (Oct. 2017).
Hampf, et al. (1990) "Sensory and autonomic measurements in idiopathic trigeminal neuralgia before and after radiofrequency thermocoagulation: differentiation from some other causes of facial pain.", *Pain*, 40:241-248.
International Search Report issued in International Patent Application No. PCT/KR2017/005172, dated Aug. 21, 2017, with English Translation.
Jeon, et al. (2012) "A novel trigeminal neuropathic pain model: Compression of the trigeminal nerve root produces prolonged nociception in rats." *Progress in Neuro-Psychopharmacology & Biological Psychiatry* 38:149-158.
Joffroy, et al. (2001) "Trigeminal neuralgia Pathophysiology and treatment." *Acta neurol. belg.*, 101:20-25.
Karakurt, et al. (2001) "Synthesis of some 1-(2-naphthyl)-2-(imidazole-1-yl)ethanone oxime and oxime ether derivatives and their anticonvulsant and antimicrobial activities." *Eur. J. Med. Chem.*, 36:421-433.
Kumar, et al. (2013) "Pain in trigeminal neuralgia: neurophysiology and measurement: a comprehensive review." *Journal of Medicine and Life*, 6(4):383-388, Oct.-Dec. 2013.
Park, et al. (2011) "Peripheral administration of NR2 antagonists attenuates orofacial formalin-induced nociceptive behavior in rats.", *Progress in Neuro-Psychopharmacology & Biological Psychiatry*, 35:982-986.

* cited by examiner

*Primary Examiner* — Jason Deck
(74) *Attorney, Agent, or Firm* — Harness, Dickey & Pierce, P.L.C.

(57) ABSTRACT

The present invention relates to a pharmaceutical composition for preventing or treating trigeminal neuralgia, the pharmaceutical composition comprising: a carbamate compound of chemical formula 1 or a pharmaceutically acceptable salt thereof, a solvate or a hydrate; and a pharmaceutically acceptable carrier. The pharmaceutical composition, according to the present invention, may enable the efficient prevention or treatment of trigeminal neuralgia.

11 Claims, 3 Drawing Sheets

USE OF CARBAMATE COMPOUND FOR PREVENTING OR TREATING TRIGEMINAL NEURALGIA

CROSS-REFERENCE TO RELATED APPLICATIONS

This application is a national phase application of PCT Application No. PCT/KR2017/005172, filed on May 18, 2017, which claims priority to Korean Patent Application No. 10-2016-0061386, filed on May 19, 2016. The entire disclosure of the applications identified in this paragraph is incorporated herein by reference.

FIELD

The present invention relates to use of a carbamate compound of the following Formula 1 for the purpose of preventing or treating trigeminal neuralgia by administering a pharmaceutical composition comprising said carbamate compound:

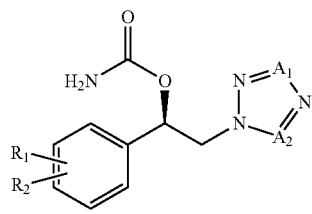

[Formula 1]

wherein,
$R_1$, $R_2$, $A_1$ and $A_2$ are as defined herein.

BACKGROUND

Pain is defined as unpleasant sensory and emotional experiences associated with actual or potential tissue injury (Pain terms: a list with definitions and notes on usage, Pain, 1979).

Trigeminal neuralgia is associated with pain from the trigeminal nerve which travels from the brain and branches to diverse part of the face. Trigeminal neuralgia causes severe, recurrent pain in the face, usually on one side. Nearly 50% of patients have a trigger zone, and many patients try to avoid stimulation in this zone because of the severe pain occurring even by a little touch there (Kumar S. et al., Pain in trigeminal neuralgia: neurophysiology and measurement, J Med Life. 2013).

The annual incidence of trigeminal neuralgia is 3 to 5 persons per 100,000 of the population and is higher in women than in men and in older people than in younger people. In the case of essential trigeminal neuralgia, it usually occurs at the age of 52 to 58 years. In cases of symptomatic trigeminal neuralgia, it usually occurs at the age of 30 to 35 years. Pain almost always occurs on one side of the face, but may occur on both sides with a frequency of 3 to 5%. It is also known that pain occurs with a frequency of 59 to 66% on the right side rather than on the left side. Pain occurs as a result of stimulating the trigger zone during routine activities such as eating, brushing teeth and talking, and it occurs frequently at any time of the day or night, and lasts for several weeks once it starts to appear (Joffroy A. et al., Trigeminal neuralgia. Pathophysiology and treatment, Acta Neurol Belg. 2001).

Pharmacological treatment and surgical treatment are performed to treat trigeminal neuralgia. Carbamazepine is the primary choice drug, and if pain continues despite the effective blood concentrations of carbamazepine, baclofen, phenytoin, etc. can be added. Side effects of carbamazepine include drowsiness, ataxia, nausea and anorexia in about 40% of patients, and may also include aplastic anemia, drug hypersensitivity, hepatic and renal toxicity, and antidiuretic hormone insufficient secretion. Approximately 30% of patients fail to control pain despite adequate pharmacological treatment (medication). In this case, surgical treatments such as alcohol injection, radiating ganglion block, Retro-Gasserian glycerol injection and microvascular decompression are performed (Joffroy A. et al., Trigeminal neuralgia. Pathophysiology and treatment, Acta Neurol Belg. 2001).

Although pharmacological treatment or surgical treatment has been adopted to treat trigeminal neuralgia, there is still a limited use due to an unsatisfactory level of efficacy or adverse effects. Hence, new drugs with improved efficacy and fewer side effects are needed.

DISCLOSURE

Problem to be Solved

The present invention is intended to provide a method for the prevention or treatment of trigeminal neuralgia.

The present invention is also intended to provide the use of a carbamate compound of the following Formula 1, or a pharmaceutically acceptable salt, solvate or hydrate thereof, for the prevention or treatment of trigeminal neuralgia:

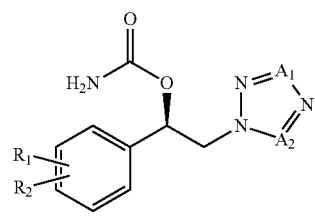

[Formula 1]

wherein,
$R_1$, $R_2$, $A_1$ and $A_2$ are as defined herein.

Technical Solution to the Problem

The present invention provides a medicament for the prevention or treatment of trigeminal neuralgia, comprising a therapeutically effective amount of a carbamate compound of the following Formula 1, or a pharmaceutically acceptable salt, solvate or hydrate thereof:

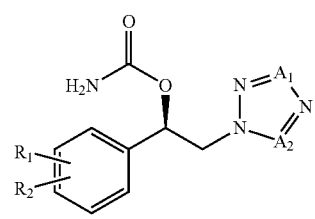

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention or treatment of trigeminal neuralgia, comprising a therapeutically effective amount of the carbamate compounds of the above Formula 1, or a pharmaceutically acceptable salt, solvate or hydrate thereof, and one or more of a pharmaceutically acceptable carrier.

In addition, the present invention provides a method for preventing or treating trigeminal neuralgia in a subject, comprising administering a therapeutically effective amount of the carbamate compounds of the above Formula 1, or a pharmaceutically acceptable salt, solvate or hydrate thereof to the subject.

In addition, the present invention provides the use of the carbamate compounds of the above Formula 1, or a pharmaceutically acceptable salt, solvate or hydrate thereof for the prevention or treatment of trigeminal neuralgia.

In one embodiment of the present invention, in the above Formula 1, R1 and R2 are each independently selected from the group consisting of hydrogen, halogen and $C_1$-$C_8$ alkyl.

In one embodiment, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

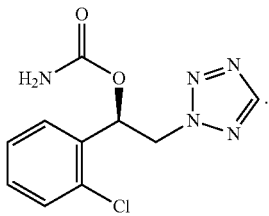

[Formula 2]

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the present invention can be chemically synthesized by any of the methods described in the above documents, but the methods are merely exemplary ones, and the order of the unit operation and the like may be selectively changed if it is necessary. Hence, the above methods are not intended to limit the scope of the invention.

The compounds of the present invention can be used for the prevention or treatment of trigeminal neuralgia.

According to the International Headache Society classification, trigeminal neuralgia is divided into two categories according to its cause and characteristics: classical trigeminal neuralgia and painful trigeminal neuropathy (International Headache Disease Classification, 3rd Edition, Beta Version, 2013).

Classical trigeminal neuralgia has no distinct cause other than neurovascular compression, and the diagnostic criteria are as follows:

(1) Unilateral facial pain occurring at least three times (2) Generation of one or more branches of the trigeminal nerve, not spreading beyond the trigeminal nerve distribution (3) Pain has at least three of the following characteristics: Repetition of sudden pain attacks lasting from one second to two minutes/severe pain/pain like electric shock, shot or stabbing, or sharp features/induced by harmless stimuli on the affected side of the face (4) No clinical evidence of neurological deficit (5) Not explained well as other diagnostics according to the International Headache Disease Classification.

Classical trigeminal neuralgia usually occurs in the second and third branches of the trigeminal nerve and never crosses to the opposite side, but rarely occurs bilaterally. After a pain attack, there is a refractory period in which pain is not felt, and when the pain is severe, it may cause contraction of the facial muscles of the affected side. The duration of a pain attack becomes longer and worse over time. Pain can induce psychosocial dysfunction and significantly reduce quality of life, often resulting in weight loss. Classical trigeminal neuralgia can be further classified into the following subtypes: (i) pure spasmodic classical trigeminal neuralgia and (ii) classical trigeminal neuralgia with persistent facial pain.

Painful trigeminal neuropathy is a condition in which pain appears in one or more areas of the trigeminal nerve branch due to other causes or nerve damage. Pain varies in appearance and strength depending on the cause.

Painful trigeminal neuropathy is classified into the following six subtypes:

(i) Painful trigeminal neuropathy due to acute shingles (herpes zoster). This refers to facial pain that occurs in one or more areas of the trigeminal nerve branch in periods of less than 3 months by acute shingles (herpes zoster).

(ii) Post-shingles trigeminal neuropathy. This refers to unilateral facial pain that exhibits various sensory changes in one or several branch areas due to shingles (herpes zoster) and occurs repeatedly for at least 3 months.

(iii) Post-painful traumatic trigeminal neuropathy. This refers to unilateral facial pain that appears and is accompanied by other symptoms or clinical signs of trigeminal nerve dysfunction after trauma in the trigeminal nerve.

(iv) Painful trigeminal neuropathy due to multiple sclerosis. This refers to unilateral facial pain that shows the characteristics of classical trigeminal neuralgia and develops in the trigeminal nerve area accompanied by other symptoms and clinical signs of multiple sclerosis.

(v) Painful trigeminal neuropathy caused by space-occupying lesions. This refers to unilateral facial pain that shows the characteristics of classical trigeminal neuralgia and develops in the trigeminal nerve area due to the involvement of the affected trigeminal nerve and the space-occupying lesions.

(vi) Painful trigeminal neuropathy due to other diseases.

Thus, the compounds of the present invention can be used for the prevention or treatment of classical trigeminal neuralgia and painful trigeminal neuropathy. The classical trigeminal neuralgia includes a pure spasmodic classical trigeminal neuralgia, a classical trigeminal neuralgia with persistent facial pain and the like. Painful trigeminal neuropathy includes painful trigeminal neuropathy due to acute shingles (herpes zoster), post-shingles trigeminal neuropathy, post-painful traumatic trigeminal neuropathy, painful trigeminal neuropathy due to multiple sclerosis, painful trigeminal neuropathy caused by space-occupying lesions, painful trigeminal neuropathy due to other diseases, and the like.

Trigeminal neuralgia shows clinical features distinct from neuropathic pain and is normal in routine clinical tests, unlike neuropathic pain. This is a criterion for diagnosing trigeminal neuralgia according to the International Headache Society. In addition, no abnormality is found in the sensory nerve examination of patients with trigeminal neuralgia (Hampf G et. al., Sensory and autonomic measurements in idiopathic trigeminal neuralgia before and after radiofrequency thermoscoagulation: differentiation from some other causes of facial pain, Pain, 1990).

The efficacy of the carbamate compounds on trigeminal neuralgia can be determined by measuring the effects on the avoidance response threshold in an animal model of trigeminal neuralgia induced by trigeminal nerve root compression or in an animal model of facial pain induced by inferior alveolar nerve injury. In addition, the efficacy of the carbamate compounds on trigeminal neuralgia can be determined by measuring the effects on the pain behavioral responses in an animal model of facial pain induced by formalin injection.

The dosage of the present compounds for the prophylactic treatment of the disease may typically vary depending on the severity of the disease, the body weight and the metabolic status of the subject. A "therapeutically effective amount" for an individual patient refers to an amount of the active compound or pharmaceutical formulation sufficient to achieve the desired pharmacological effect, i.e., the prophylactic therapeutic effect as described above. The therapeutically effective amount of the compounds of the present invention is 50 to 500 mg, preferably 50 to 400 mg, more preferably 50 to 300 mg, and more preferably 50 to 200 mg, based on once-daily administration to humans.

The compounds of the present invention may be administered by a conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the present compounds, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphtoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, diethyleneamine, meglumine, procaine, aluminum, ammonium, tetramethylammonium, calcium lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention can be formulated such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skills can easily determine and prescribe dosages that are effective for the desired treatment or prophylaxis. The medicament or pharmaceutical composition according to one embodiment may be administered in one or more doses, for example, one to four times per day. The pharmaceutical composition according to one embodiment may contain 50 to 500 mg, preferably 50 to 400 mg, more preferably 50 to 300 mg, and more preferably 50 to 200 mg of the compound of Formula 1.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "treat," "treating" and "treatment" refer to eliminating or alleviating a disease and/or its accompanying symptoms altogether or in part.

As used herein, the term "subject" refers to an animal that is the object of prevention or treatment, preferably a mammal (e.g., primates (e.g., a human), cattle, sheep, goats, horses, dogs, cats, rabbits, rats, mice, etc.), most preferably a human.

Effect of the Invention

The carbamate compounds of the present invention show significant effects on the avoidance response threshold not only in the animal models of trigeminal neuralgia but also in the animal models of facial pain induced by inferior alveolar nerve injury, and significantly reduce the pain behavioral response in the animal models of facial pain induced by formalin injection. Hence, the pharmaceutical composition according to the present invention can effectively prevent and treat trigeminal neuralgia.

DETAILED DESCRIPTION

Figure 1:
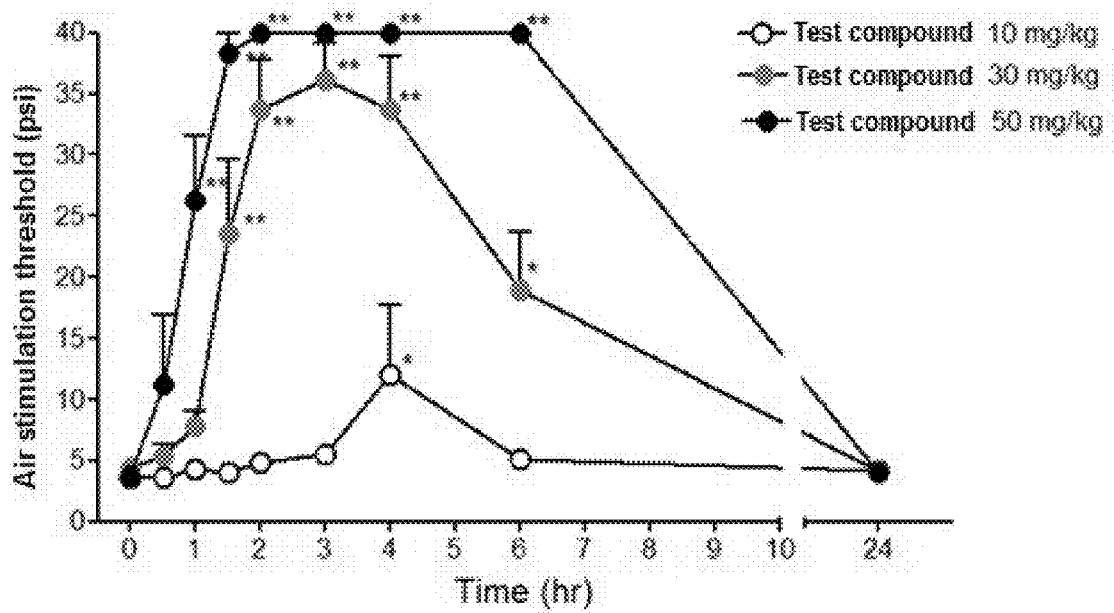
FIG. 1 shows the effect of the test compound on the air stimulation avoidance response threshold over time after administration of the test compound to rats in which trigeminal neuralgia was induced by the trigeminal nerve root compression.

Hereinafter, the present invention will be explained in more detail through working examples. However, the following working examples are only intended to illustrate one or more embodiments and are not intended to limit the scope of the invention.

Synthesis Example: Synthesis of carbamic acid (R)-1-(2-chlorophenyl)-2-tetrazol-2-yl-ethyl ester Carbamic acid (R)-1-(2-chlorophenyl)-2-tetrazol-2-yl-ethyl ester (hereinafter referred to as "the test compound") was prepared according to the method described in Synthesis Example 50 of PCT Publication No. WO 2010/150946.

Example 1: Effect on Trigeminal Neuralgia Induced by Trigeminal Nerve Root Compression Experimental Animals Mature male rats (Sprague-Dawley, 200-230 g) were used. The experimental animals were maintained under conditions of light-and-darkness cycle of 12 hours, a temperature of 22 to 25° C., a relative humidity of 40 to 60%, and free access to water and food.

Induction of Trigeminal Neuralgia

Rats were anesthetized with a mixed solution of ketamine (40 mg/kg) and xylazine (4 mg/kg), fixed on a stereotaxic instrument, and 4% agar solution was injected into the left trigeminal nerve roots using a stainless steel injection tube to compress the trigeminal nerve roots. 10 μl of 4% agar solution was slowly injected over the trigeminal nerve roots for 5 seconds, and the injection tube was removed after 5 minutes and then sutured (Jeon H J. et. al., A novel trigeminal neuropathic pain model: compression of the trigeminal nerve root produces prolonged nociception in rats, Prog Neuropsychopharmacol Biol Psychiatry. 2012).

Measurement of Mechanical Allodynia

To observe the behavioral response, the animals were placed in a cage and adapted for 20 minutes in a quiet area, followed by an air-puff test to assess mechanical allodynia to air stimulation. Aggressive behaviors such as head movement to avoid air stimulation or biting in response to the air stimulation applied to the facial region which is dominated by the trigeminal nerve were used as evaluation criteria for the behavioral reflex. A total of 10 trials and 50% or more responses were considered as the threshold of stimulation. Stimulation was stopped when the response did not appear even after stimulation of 40 psi or greater.

Administration

On the 7th day after surgery, the test compound (10, 30 and 50 mg/kg) and carbamazepine (25 and 50 mg/kg) were intraperitoneally administered to the test animals in which allodynia had been induced. At 30 minutes, 60 minutes, 90 minutes, 2 hours, 3 hours, 4 hours and 6 hours after administration, the pharmacological effects of the drugs were evaluated by observing changes in the behavioral responses.

Statistics

The effect of the compounds was expressed as mean±standard error, and statistical significance was recognized when data were $p<0.05$ difference using one-way ANOVA and Dunnett's test.

The trigeminal nerve roots were compressed with agar to induce pain similar to trigeminal neuralgia occurring in the human body. The experimental animals in which trigeminal nerve roots were compressed showed a significant pain response, and this pain was maintained over about 40 days after nerve compression surgery.

Figure 2:
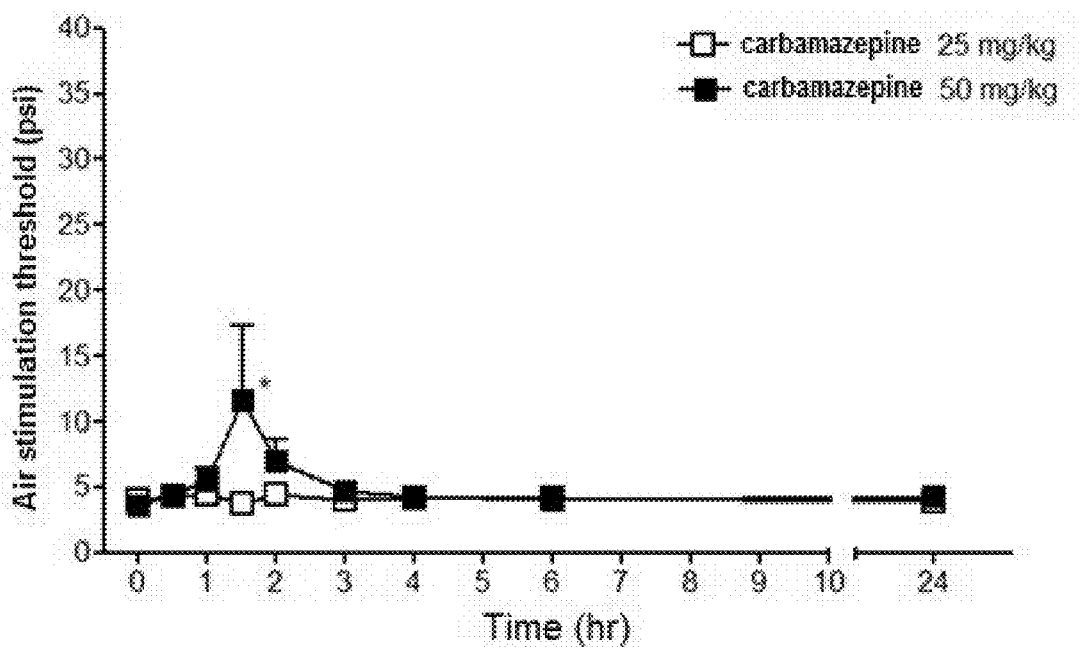
FIG. 2 shows the effect of carbamazepine on the air stimulation avoidance response threshold over time after administration of carbamazepine to rats in which trigeminal neuralgia was induced by the trigeminal nerve root compression.

As can be seen from FIG. 1, the intraperitoneal administration of the test compound at 30 and 50 mg/kg significantly inhibited the mechanical allodynia induced by trigeminal nerve root compression. In the case of the test compounds (30 and 50 mg/kg), analgesic effect could be observed from 60 minutes after administration, and this effect was confirmed to be maintained for 6 hours after administration. In the case of carbamazepine, a dose of 25 mg/kg showed no analgesic effect, whereas a dose of 50 mg/kg showed a transient low analgesic effect (FIG. 2).

As described above, the test compound showed a statistically significant effect in the trigeminal neuralgia animal model and exhibited better analgesic action than carbamazepine.

Example 2: Effect on Facial Pain Induced by Inferior Alveolar Nerve Injury

Experimental Animals

Mature male rats (Sprague-Dawley, 200-230 g) were used. The experimental animals were maintained under conditions of light-and-darkness cycle of 12 hours, a temperature of 22 to 25° C., a relative humidity of 40 to 60%, and free access to water and food.

Induction of Trigeminal Neuralgia

The rats were anesthetized with a mixed solution of ketamine (40 mg/kg) and xylazine (4 mg/kg), then the left second molar of the lower jaw was extracted, and a small dental implant was implanted abnormally to induce inferior alveolar nerve injury (Han S R. et. al., Early dexamethasone relieves trigeminal neuropathic pain, J Dent Res. 2010).

Measurement of Mechanical Allodynia

To observe the behavioral response, the animals were placed in a cage and adapted for 20 minutes in a quiet area, followed by an air-puff test to assess mechanical allodynia to air stimulation. Aggressive behaviors such as head movement to avoid air stimulation or biting in response to the air stimulation applied to the facial region which is dominated by the trigeminal nerve were used as evaluation criteria for the behavioral reflex. A total of 10 trials and 50% or more responses were considered as the threshold of stimulation. Stimulation was stopped when the response did not appear even after stimulation of 40 psi or greater.

Administration

On the 7th day after surgery, the test compound (5, 10 and 20 mg/kg) and carbamazepine (25 and 50 mg/kg) were intraperitoneally administered to the test animals in which allodynia had been induced. At 30 minutes, 60 minutes, 90 minutes, 2 hours, 3 hours, 4 hours and 6 hours after administration, the pharmacological effects of the drugs were evaluated by observing changes in the behavioral responses.

Statistics

The effect of the compounds was expressed as mean±standard error, and statistical significance was recognized when data were p<0.05 difference using one-way ANOVA and Dunnett's test.

The experimental animals with inferior alveolar nerve injury showed a significant pain response, and recovery from the pain occurred in about 40 days after nerve compression surgery.

Figure 3:
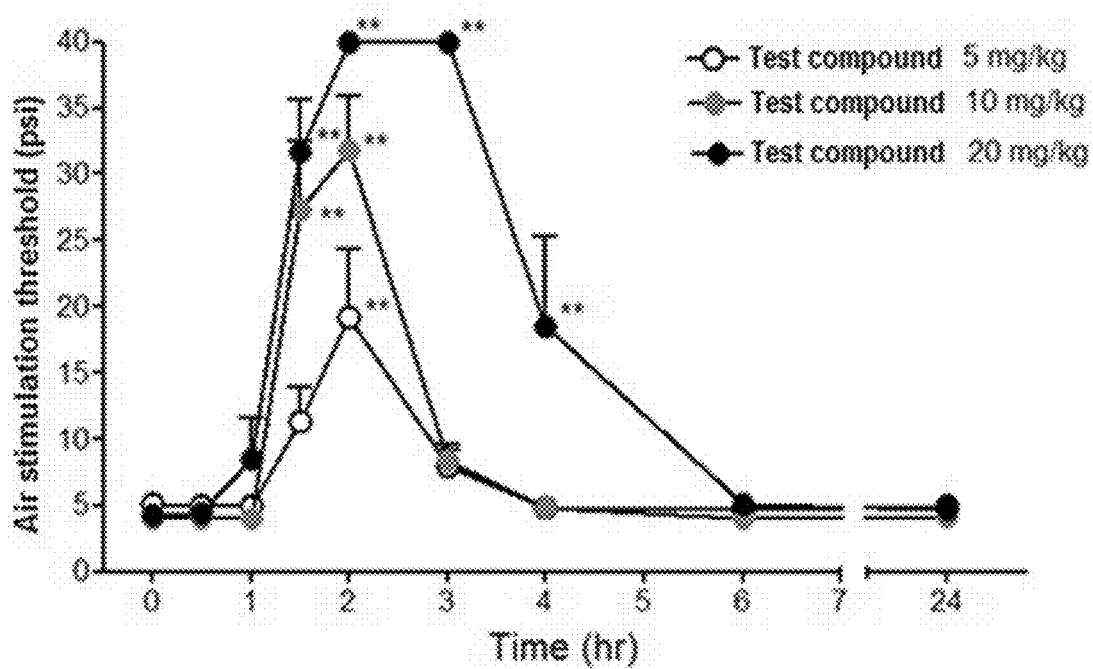
FIG. 3 shows the effect of the test compound on the air simulation avoidance response threshold over time after administration of the test compound to rats in which facial pain was induced by inferior alveolar nerve injury.
Figure 4:
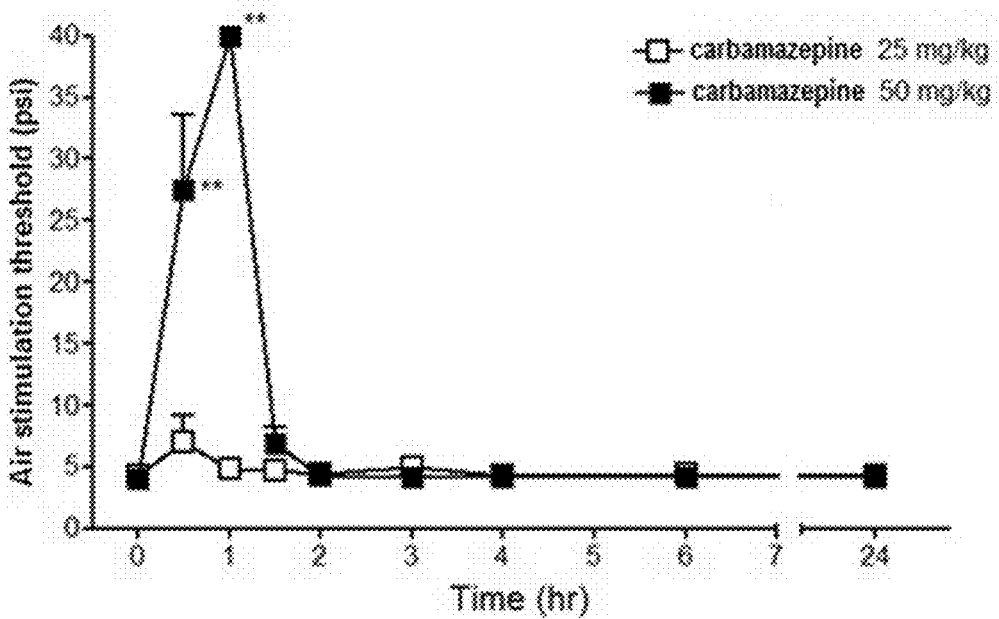
FIG. 4 shows the effect of carbamazepine on the air simulation avoidance response threshold over time after administration of carbamazepine to rats in which facial pain was induced by inferior alveolar nerve injury.

As can be seen from FIG. 3, the intraperitoneal administration of the test compound at 5, 10 and 20 mg/kg significantly inhibited the mechanical allodynia induced by inferior alveolar nerve injury. When the test compound was intraperitoneally administered at a dose of 20 mg/kg, a significant pain-relieving effect was observed from 90 minutes after administration, and this effect was confirmed to be maintained for 4 hours. When the test compound was administered at doses of 5 and 10 mg/kg, it was confirmed that the effect was significant from 90 minutes to 2 hours after administration. In the case of carbamazepine, a dose of 25 mg/kg showed no analgesic effect, whereas a dose of 50 mg/kg showed a significant analgesic effect, but the analgesic effect completely disappeared 2 hours after administration (FIG. 4).

As described above, the test compound showed a statistically significant effect in the inferior alveolar nerve injury-induced facial pain model, and exhibited an analgesic action equivalent to or greater than carbamazepine and lasted longer than carbamazepine.

Example 3: Effect on Facial Pain Induced by Formalin

Experimental Animals

Mature male rats (Sprague-Dawley, 200-230 g) were used. The experimental animals were maintained under conditions of light-and-darkness cycle of 12 hours, a temperature of 22 to 25° C., a relative humidity of 40 to 60%, and free access to water and food.

Injection of Formalin and Measurement of Pain Behavior

5% Formalin (50 µl) was injected subcutaneously into the vibrissa pad on the left facial area of the rats using an insulin syringe (31 gauge). The behavioral response of rubbing or scratching the maxillofacial area was observed from 10 minutes after injection, accumulating in a unit of 5 minutes, for a total of 35 minutes (Park M K. et. al., Peripheral administration of NR2 antagonists attenuates orofacial formalin-induced nociceptive behavior in rats, Prog Neuropsychopharmacol Biol Psychiatry, 2011).

Administration

The vehicle, the test compound (5 and 20 mg/kg) and carbamazepine (25 mg/kg) were intraperitoneally administered, and after 30 minutes 5% formalin was injected into the left facial area.

Statistics

The effect of the compounds was expressed as mean±standard error, and statistical significance was recognized when data were p<0.05 difference using one-way ANOVA and Dunnett's test.

When formalin was injected subcutaneously into the vibrissa pad on the facial area of the rats, the pain behavioral response of scratching the facial area lasted for 45 minutes. This reaction was divided into the first response (first phase) which occurs rapidly and readily for 10 minutes from immediately after injection and the second response (second phase) which continues over a long period of time for 10 to 45 minutes.

Figure 5:
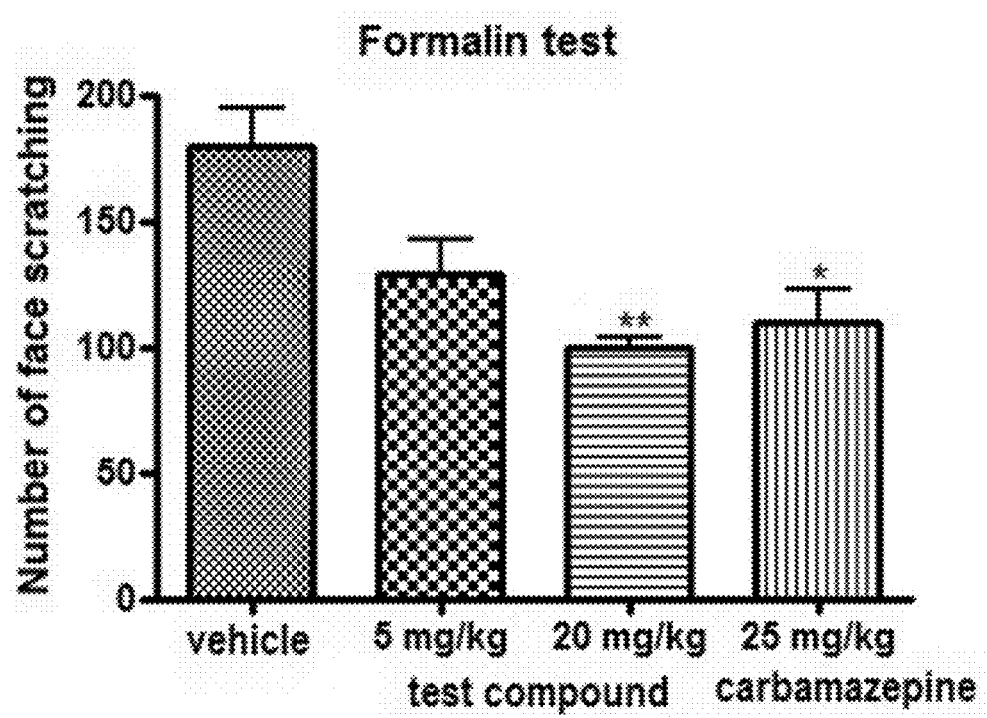
FIG. 5 shows the effects of the test compound and carbamazepine on the formalin-induced pain behavioral response in rats after administration of the test compound and carbamazepine.

As can be seen from FIG. 5, the intraperitoneal administration of the test compound at doses of 5 and 20 mg/kg showed a statistically significant decrease in the pain behavioral response as compared with the vehicle-administered group, and a similar effect was observed in the carbamazepine 25 mg/kg administered group.

From the above results, it could be understood that the test compound shows significant effects not only in the trigeminal neuralgia disease model but also in the facial pain caused by lower mitral nerve injury and formalin injection, and that it has an equal or greater effect than carbamazepine, which is used as a therapeutic agent for patients with trigeminal neuralgia.

What is claimed is:

1. A method for preventing or treating trigeminal neuralgia in a subject, comprising:
   administering a therapeutically effective amount of a carbamate compound of Formula 1, or a pharmaceutically acceptable salt, solvate or hydrate thereof to the subject:

[Formula 1]

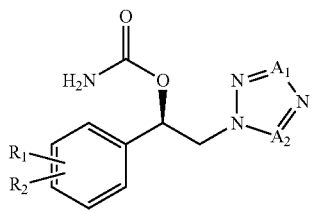

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl-ethyl ester of Formula 2:

[Formula 2]

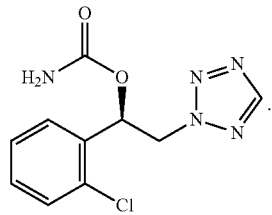

4. The method according to claim 1, wherein the trigeminal neuralgia is a classical trigeminal neuralgia.

5. The method according to claim 4, wherein the classical trigeminal neuralgia is pure spasmodic classical trigeminal neuralgia or classical trigeminal neuralgia with persistent facial pain.

6. The method according to claim 1, wherein the trigeminal neuralgia is a painful trigeminal neuropathy.

7. The method according to claim 6, wherein the painful trigeminal neuropathy is painful trigeminal neuropathy due to acute shingles (herpes zoster), post-shingles trigeminal neuropathy, post-painful traumatic trigeminal neuropathy, painful trigeminal neuropathy due to multiple sclerosis, painful trigeminal neuropathy caused by space-occupying lesions, or painful trigeminal neuropathy due to other diseases.

8. The method according to claim 1, wherein the subject is a mammal.

9. The method according to claim 8, wherein the mammal is a human.

10. The method according to claim 1, wherein the therapeutically effective amount of the carbamate compound of Formula 1 is 50 mg to 500 mg based on once-daily administration.

11. The method according to claim 1, wherein the carbamate compound of Formula 1, or a pharmaceutically acceptable salt, solvate or hydrate thereof is administered orally, parenterally, intravenously, intramuscularly, subcutaneously or rectally.

* * * * *